(12) United States Patent
Tu et al.

(10) Patent No.: US 7,304,180 B2
(45) Date of Patent: Dec. 4, 2007

(54) PROCESS FOR PRODUCING METAL OXIDE CATALYST

(75) Inventors: Xinlin Tu, Nagoya (JP); Yuuichi Sumida, Nagoya (JP); Mamoru Takahashi, Nagoya (JP); Hiroshi Niizuma, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 10/542,804

(22) PCT Filed: Jan. 20, 2004

(86) PCT No.: PCT/JP2004/000427

§ 371 (c)(1),
(2), (4) Date: Jul. 20, 2005

(87) PCT Pub. No.: WO2004/065004

PCT Pub. Date: Aug. 5, 2004

(65) Prior Publication Data

US 2006/0047137 A1    Mar. 2, 2006

(30) Foreign Application Priority Data

Jan. 21, 2003    (JP) ............................. 2003-011805

(51) Int. Cl.
*C07C 51/16*    (2006.01)
*B01J 23/28*    (2006.01)
*B01J 23/00*    (2006.01)

(52) U.S. Cl. ...................... 562/547; 502/248; 502/255; 502/311; 502/312; 502/313; 502/314; 502/315; 502/316; 502/317; 502/321; 502/322

(58) Field of Classification Search ................ 502/248, 502/255, 311, 312, 313–317, 321–322; 558/338; 562/547

See application file for complete search history.

(56) References Cited

U.S. PATENT DOCUMENTS

| 5,994,580 | A | * | 11/1999 | Takahashi et al. | ......... 562/549 |
|---|---|---|---|---|---|
| 6,060,422 | A | * | 5/2000 | Takahashi et al. | .......... 502/312 |
| 6,291,393 | B1 | * | 9/2001 | Tu et al. | ..................... 502/311 |
| 6,346,647 | B2 | * | 2/2002 | Tu et al. | ..................... 562/549 |
| 6,432,870 | B1 | * | 8/2002 | Tu et al. | ..................... 502/305 |
| 6,461,996 | B2 | * | 10/2002 | Chaturvedi et al. | ......... 502/312 |
| 6,512,141 | B2 | * | 1/2003 | Tu et al. | ..................... 562/549 |
| 2002/0072628 | A1 | * | 6/2002 | Tu et al. | ..................... 562/545 |
| 2002/0183547 | A1 | * | 12/2002 | Gaffney et al. | ............. 562/546 |
| 2002/0183548 | A1 | * | 12/2002 | Bogan et al. | ................ 562/546 |
| 2003/0004379 | A1 | * | 1/2003 | Gaffney et al. | ............. 568/910 |
| 2003/0176734 | A1 | * | 9/2003 | Chaturvedi et al. | ......... 562/547 |
| 2003/0208085 | A1 | * | 11/2003 | Gaffney et al. | ............. 558/321 |
| 2004/0019233 | A1 | * | 1/2004 | Bogan et al. | ................ 558/323 |
| 2004/0116731 | A1 | * | 6/2004 | Gaffney et al. | ............. 558/320 |
| 2004/0176244 | A1 | * | 9/2004 | Bogan et al. | ................ 502/208 |
| 2004/0181085 | A1 | * | 9/2004 | Bogan et al. | ................ 558/323 |

FOREIGN PATENT DOCUMENTS

JP    11-226408 A    8/1999

OTHER PUBLICATIONS

Edited by Kagaku Kogaku Kyokai Kagaku Kogaku Binran, Dai 3 Han, May 10, 1068, pp. 1024-1033, 1450 International Search Report dated May 11, 2004.

* cited by examiner

*Primary Examiner*—Cam N. Nguyen
(74) *Attorney, Agent, or Firm*—Sughrue Mion, PLLC

(57) ABSTRACT

The invention relates to a process for producing a metal oxide catalyst capable of producing acrylic acid, acrylonitrile or the like in one stage by catalytic oxidation reaction of propane in a high yield.

The invention is characterized by using one obtained by finely ground metallic Te or metallic Sb in water or an organic solvent as a raw material for the production of an oxide catalyst made of metal elements Mo—V—Nb—Te or metal elements Mo—V—Nb—Sb. The powder of the metallic Te or metallic Sb obtained by grinding preferably has a mode size of not more than 20 μm. By using the metal oxide obtained by the invention as a catalyst, it is possible to produce acrylic acid in a high yield of 35% or more from propane by a one-stage oxidation reaction.

8 Claims, No Drawings

PROCESS FOR PRODUCING METAL OXIDE CATALYST

TECHNICAL FIELD

The present invention relates to a process for producing a metal oxide catalyst which is used in the production of acrylic acid by vapor phase catalytic oxidation of propane, the production of acrylonitrile by ammoxidation of propane and the like.

BACKGROUND ART

In general, acrylic acid is produced by a two-stage oxidation reaction of undergoing catalytic reaction of propylene with oxygen in the presence of a catalyst to produce acrlolein and undergoing catalytic reaction of the resulting acrlolein with oxygen.

On the other hand, in the recent years, due to a price difference between propane and propylene and for the purpose of overcoming problems such as complexity in process involving the two-stage oxidation, a process for producing acrylic acid in one stage by using propane as a starting material is studied, and there have been made a number of proposals with respect to catalysts to be used therefor. As representative examples thereof, there are enumerated catalysts made of a composite metal oxide such as [V, P, Te] bases, [Mo, Te, V, Nb] bases, and [Mo, Sb, V, Nb] bases.

Recently, there have been filed some applications for patent with respect to improvements of the foregoing metal oxide catalysts. That is, JP-A-10-137585 discloses a process for producing a catalyst by mixing a reaction aqueous solution obtained by allowing a molybdenum compound, a vanadium compound and an antimony compound to react in an aqueous medium at 70° C. or higher with a niobium compound, evaporating to dryness the resulting mixture, and further calcining it at a high temperature.

JP-A-10-230164 describes that in heat treating the respective metal compounds in the aqueous medium described in the foregoing patent document, a gas containing molecular oxygen is introduced into the aqueous medium and that when the catalyst as produced in this process is used for vapor phase oxidation reaction of propane, the yield of acrylic acid is further enhanced.

Also, JP-A-11-285636 describes a method for adding hydrogen peroxide to a reaction liquid of the respective metal compounds under heating and reaction or a reaction liquid thereof after the reaction in the aqueous medium as described in the foregoing JP-A-10-137585 and JP-A-10-230164.

However, even in the case of using the catalysts as described in the foregoing patent documents, the yield of acrylic acid in a one-stage oxidation reaction of propane does not reach a practical level required in the acrylic acid production.

JP-A-11-226408 discloses a method for allowing a metal powder to react with an oxometalate of other element and using a reaction liquid having the metal powder substantially dissolved therein as a raw material in the production of a catalyst. In this method, it is described that for the purpose of accelerating the reaction of the metal powder having a small dissolution rate, heating is carried out over a long period of time and that an oxidizing agent is added. However, JP-A-11-226408 does not provide any description with respect to a grinding treatment of the metal powder.

DISCLOSURE OF THE INVENTION

In order to obtain a catalyst capable of producing acrylic acid, acrylonitrile or the like in one stage by catalytic oxidation reaction of propane in a high yield, the present inventors made extensive and intensive investigations. As a result, it has been found that the foregoing problems can be solved by using one prepared by finely grinding Te or Sb as a raw material in the production of a metal oxide catalyst in water or an organic solvent, leading to accomplishment of the invention. Accordingly, an object of the invention is to provide a process for producing a metal oxide catalyst upon which the foregoing problems are solved.

The invention of achieving the foregoing object is concerned with a process for producing a metal oxide catalyst represented by the following composition formula, which is characterized by using, as a raw material, a fine particle dispersion of metallic Te or Sb obtained by grinding the following metallic Te or Sb in the presence of water or an organic solvent not containing any of $Mo^{6+}$ compounds and $V^{5+}$ compounds.

Composition formula:

(In the formula, A is Te or Sb; and B is at least one element selected from the group consisting of Nb, Ta, W, Ti, Zr, Re, Fe, Ni, Co, Sn, Tl, Cu, rare earth elements, and alkali metal elements. $\underline{i}$ and $\underline{j}$ are each from 0.01 to 1.5, and j/i is from 0.3 to 1.0; $\underline{k}$ is from 0.001 to 3.0; and $\underline{y}$ is the number to be determined by the oxidized state of other elements.)

Also, the invention is concerned with a process for producing a metal oxide catalyst represented by the following composition formula, which is characterized by employing a process comprising the following step (1), step (2), step (3) and step (4).

Step (1): A step in which the following metal A is ground in the presence of water or an organic solvent not containing any of $Mo^{6+}$ compounds and $V^{5+}$ compounds;

Step (2): A step in which in the case where an aqueous dispersion has been obtained in the foregoing step (1), an aqueous dispersion resulting from adding an $Mo^{6+}$ compound and a $V^{5+}$ compound to the subject aqueous dispersion is heated at 60° C. or higher for at least 10 minutes, or in the case where an organic solvent dispersion has been obtained in the step (1), an aqueous dispersion resulting from adding an $Mo^{6+}$ compound and a $V^{5+}$ compound to an aqueous dispersion obtained by substituting the organic solvent with water is heated at 60° C. or higher for at least 10 minutes;

Step (3): A step in which a compound containing the following metal B is added to a reaction liquid obtained in the foregoing step (2); and Step (4): A step in which a dried material obtained by evaporating to dryness a mixed liquid obtained in the foregoing step (3) is dried and further calcined.

Composition formula:

(In the formula, A is Te or Sb; and B is at least one element selected from the group consisting of Nb, Ta, W, Ti, Zr, Re, Fe, Ni, Co, Sn, Tl, Cu, rare earth elements, and alkali metal elements. $\underline{i}$ and $\underline{j}$ are each from 0.01 to 1.5, and j/i is from 0.3 to 1.0; $\underline{k}$ is from 0.001 to 3.0; and $\underline{y}$ is the number to be determined by the oxidized state of other elements.)

Further, the invention is concerned with a process for producing acrylic acid or acrylonitrile, which is characterized by subjecting propane to oxidation by vapor phase catalytic reaction or ammoxidation in the presence of the metal oxide catalyst as produced by the foregoing processes.

BEST MODE FOR CARRYING OUT THE INVENTION

The process for producing a metal oxide catalyst of the invention will be hereunder described while dividing into steps (1) to (4).

(Step 1)

In the process for producing a metal oxide catalyst of the invention, a metal A as a raw material of the catalyst, that is, metallic Te or metallic Sb, is ground and dispersed. The raw material metal A is preferably one in a particulate form. Specifically, one having a particle size of not more than 200 μm is preferable because it is easily ground.

The grinding of the metal A is carried out in the presence of water or an organic solvent. Water or an organic solvent which does not contain any of $Mo^{6+}$ compounds and $V^{5+}$ compounds (hereinafter sometimes referred to as "specific metal compounds") is used. The case where the metal A is ground in water or an organic solvent containing these specific metal compounds is already filed as an application for patent (Japanese Patent Application No. 2002-360492).

Though the organic solvent which is used during grinding is not particularly limited, organic solvents which are liquid at the ambient temperature and can be easily removed in a post step are preferable. Specifically, alcohols such as methanol, ethanol, and propanol, and hydrocarbons such as hexane, cyclohexane, and toluene are preferable. When water or the organic solvent is co-present at the time of grinding, an increase of the surface energy accompanying the grinding is relieved, and grinding efficiency is enhanced.

With respect to a mixing proportion of water or the organic solvent to the metal A at the time of grinding, water or the organic solvent is preferably used in an amount of from 10 to 1,000 parts by mass, and more preferably from-30 to 300 parts by mass based on 100 parts by mass of the metal A. When the mixing proportion of water or the organic solvent to the metal A is less than 10 parts by mass, the metal A adheres to a grinding vessel so that the grinding becomes difficult. Also, when it exceeds 1,000 parts by mass, the solvent absorbs the impact during the grinding so that grinding efficiency is lowered.

For a grinding machine, a mode by which grinding is conducted by driving the vessel containing the material to be ground to roll is preferable. Specifically, there are enumerated a ball mill, a vibration mill, a planetary ball mill, and the like. A grinding time is suitably from 0.5 to 24 hours.

By the foregoing grinding treatment, a dispersion having the metal A dispersed in water or an organic solvent is obtained. The metal A powder in the dispersion preferably has a mode size (a particle size region where when a particle size distribution of the powder is measured, the largest amount of powders are contained) of not more than 20 μm, and more preferably from 15 to 0.6 μm. The mode size of the metal A becomes smaller by a heating step as described later, and it is preferable that the particle size of the metal A powder after that heating step becomes not more than 0.1 μm. On the other hand, in the case where the mode size of the metal A powder after grinding exceeds 20 μm, the metal A powder having a mode size of 0.5 μm or more remains even after completion of the heating step, thereby lowering the performance of the metal oxide catalyst as ultimately produced.

In the foregoing grinding treatment, it is preferred to further add aqueous solution of hydrogen peroxide to water or the organic solvent. With the presence of aqueous solution of hydrogen peroxide, the performance of the resulting metal oxide catalyst is more enhanced. Though the details of the mechanism for the enhanced catalytic performance generated by the addition of aqueous solution of hydrogen peroxide are not clarified yet at present, it is assumed that with the presence of aqueous solution of hydrogen peroxide in water or the organic solvent, dispersion of the metal A powder in the resulting dispersion is stabilized, the high dispersion state is kept without causing sedimentation, and this gives preferable influences in the production of the metal oxide catalyst.

An addition amount of aqueous solution of hydrogen peroxide to be added to water or the organic solvent is preferably from 0.1 to 3.0 moles, and more preferably from 0.3 to 1.5 moles per mole of the metal A. When the addition amount of hydrogen peroxide is less than 0.1 moles, the enhancement of the performance of the resulting metal oxide catalyst is small, whereas when the addition amount of hydrogen peroxide exceeds 3.0 moles, the metal A powder is completely dissolved in the heating step as described later so that the performance of the resulting metal oxide catalyst is lowered.

(Step 2)

In the case where an aqueous dispersion of the metal A has been obtained in the foregoing step (1), an $Mo^{6+}$ compound and a $V^{5+}$ compound are added to the subject aqueous dispersion.

In the case where an organic solvent dispersion of the metal A has been obtained in the foregoing step (1), the organic solvent is substituted with water, and an $Mo^{6+}$ compound and a $V^{5+}$ compound are added to an aqueous dispersion of the metal A as obtained by the substitution. Examples of a method for substituting the organic solvent with water include a method by distilling off the organic solvent from the organic solvent dispersion in vacuo and a method by removing the organic solvent with a centrifugation operation and then redispersing the residue in water. Incidentally, it is not necessary to completely remove the organic solvent. In the case where the content of the organic solvent in the aqueous dispersion is less than 3%, there is not substantially generated a problem. When a water-soluble alcohol is used as the organic solvent, an aqueous dispersion may be prepared by adding water to an alcohol-containing dispersion.

Examples of the $Mo^{6+}$ compound include ammonium molybdate, molybdenum oxide, and molybdic acid. Of these compounds, ammonium molybdate is preferable because it is water-soluble. Also, as the $V^{5+}$ compound, ammonium metavanadate, vanadium pentoxide, and the like are preferable.

The addition amount of each the $Mo^{6+}$ compound and the $V^{5+}$ compound is from 0.01 to 1.5 in terms of an atomic ratio of V and the metal A (i and j) based on Mo, and an atomic ratio of the metal A to V (j/i) is from 0.3 to 1.0.

When the proportions of Mo, V and the metal A fall outside the foregoing ranges, a metal oxide catalyst having an expected performance cannot be obtained.

Next, the aqueous dispersion having the $Mo^{6+}$ compound and the $V^{5+}$ compound added thereto is subjected to heat treatment. For the purpose of improving the operability or other purpose, the aqueous dispersion may be diluted by the addition of water as the need arises. With respect to the heating condition, the heating is carried out at 60° C. or higher, and preferably at from 70 to 100° C. preferably for from 10 minutes to 10 hours, and more preferably for from 30 minutes to 3 hours. It is preferred to stir the aqueous dispersion during heating.

By adding the $Mo^{6+}$ compound and the $V^{5+}$ compound to the aqueous dispersion of the ground metal A fine particle and heating the mixture under the foregoing condition, a deeply blue reaction liquid in which the metal A fine particle having a particle size of not more than 100 nm is stably dispersed is obtained.

When the heating temperature or heating time falls outside the foregoing range, the metal A is liable to cause excessive reaction. As an example of the excessive reaction, in the case of using Te as the metal A, tellurium dioxide which is insoluble in water is formed, resulting in a reduction of the performance of the resulting metal oxide catalyst.

(Step 3)

In the step (3), a compound containing a metal B is added to the reaction liquid as obtained via the foregoing steps (1) and (2). By this addition operation, a fine precipitate is formed in the reaction liquid. Though the reaction temperature is not particularly limited, the reaction temperature is usually at room temperature.

The metal B is at least one element selected from the group consisting of Nb, Ta, W, Ti, Zr, Re, Fe, Ni, Co, Sn, Tl, Cu, rare earth elements, and alkali metal elements.

Examples of the B-containing compound which can be used in the invention include oxides, nitrates, carboxylates, oxometalates, and oxalates. The insoluble B-containing compound may be dispersed in water and provided for use. In this case, by jointly using oxalic acid, etc., the compound can be dissolved in water.

An addition amount of the B-containing compound is an amount such that when Mo is defined as 1, the metal B is from 0.001 to 3 in terms of an atomic ratio in the resulting metal oxide catalyst. In the subject catalyst, in the case where when Mo is defined as 1, the proportion of the metal B is less than 0.001, deterioration of the resulting catalyst is liable to occur. On the other hand, in the case where it exceeds 3.0, the activity of the resulting catalyst becomes low, and the conversion of propane is inferior.

In the step (3), by adding ammonium nitrate and ammonia water together with the B-containing compound to the reaction liquid as obtained via the step (2), the catalytic performance of the resulting metal oxide is enhanced. With respect to preferred use amounts of ammonium nitrate and ammonia water, the amount of ammonia water is an amount containing 0.4 or more of ammonia in terms of a molar ratio to the metal B, and the amount of ammonium nitrate is an amount containing 2.0 or more of a nitric acid ion in terms of a molar ratio to the metal B, respectively.

(Step 4)

In the step (4), the mixed liquid (slurry) as obtained via the foregoing step (3) is evaporated to dryness, and the resulting dried material is dried and then calcined. For the sake of removing a large amount of water as contained, the foregoing mixed liquid can be dried by a conventionally known method such as evaporation to dryness and spray drying. In the case of evaporation to dryness, though the water may be evaporated merely by heating, when a method for blowing an inert gas such as nitrogen and air is employed, it is possible to efficiently achieve evaporation to dryness. A temperature of the evaporation to dryness is preferably in the range of from 50 to 130° C.

Next, the dried material as obtained by the foregoing operation is first calcined at a temperature of from 250 to 380° C., and preferably from 280 to 330° C. for from 2 to 20 hours, and preferably from 3 to 10 hours in the presence of oxygen. Thereafter, the resulting material is further calcined at a temperature of from 500 to 660° C., and preferably from 570 to 620° C. for from 0.5 to 6 hours, and preferably from 1 to 3 hours in the absence of oxygen.

In the invention, it is preferred to obtain a metal oxide catalyst represented by the following composition formula by this two-stage calcining.

Composition formula:

(In the formula, A is Te or Sb; and B is at least one element selected from the group consisting of Nb, Ta, W, Ti, Zr, Re, Fe, Ni, Co, Sn, Tl, Cu, rare earth elements, and alkali metal elements. i and j are each from 0.01 to 1.5, and j/i is from 0.3 to 1.0; k is from 0.001 to 3.0; and y is the number to be determined by the oxidized state of other elements.)

Incidentally, the determination of the contents of metal elements in the metal oxide catalyst as obtained by the foregoing calcining can be carried out by fluorescent X-ray analysis.

The metal oxide catalyst as obtained by the foregoing method can be used as it is. However, it is preferable that the metal oxide catalyst is ground in an appropriate particle size, thereby increasing a surface area of the catalyst and then provided for use. As grinding methods, any method of a dry-type grinding method and a wet-type grinding method can be employed.

Specific examples of a grinding device include a mortar and a ball mill. In the case of wet-type grinding, as grinding assistants, water, alcohols, and the like are enumerated.

In the case where the present catalyst is ground and used, its particle size is preferably not more than 20 μm, and more preferably not more than 5 μm.

Though the metal oxide catalyst can be used in a non-supported state, it can also be used by supporting on a known carrier having an appropriate particle size, such as silica, alumina, silica-alumina, and silicon carbide. The supporting amount is not particularly limited but follows a conventional supporting amount.

Next, the vapor phase catalytic oxidation reaction method of propane using the metal oxide catalyst as produced by the foregoing production process will be hereunder described.

Propane and oxygen as raw materials of the production of acrylic acid are introduced into a reactor charged with the foregoing metal oxide catalyst and catalytically oxidized by the metal oxide catalyst, thereby producing acrylic acid.

Propane and oxygen may be separately introduced into a reactor, the both of which are then mixed within the reactor; and the both may be mixed in advance and then introduced into a reactor. Examples of oxygen include a pure oxygen gas and air, or a diluted gas thereof with nitrogen, steam or carbon dioxide. In the case where propane and air are used as raw materials, a use proportion of air to propane is preferably not more than 30 times, and more preferably from 0.2 to 20 times in terms of a volume ratio. Though the unreacted raw material propane present in a reaction gas to be discharged from an outlet of the reactor or propylene as an intermediate can be used as a fuel as it is, the unreacted raw material propane or propylene as an intermediate which has been separated from other components in the reaction gas can be returned into the reactor and reused.

A reaction temperature is preferably from 300 to 600° C., and more preferably from 350 to 500° C.

A space velocity (hereinafter referred to as "SV") of the raw material gas is suitably from 1,000 to 8,000 hr$^{-1}$. When the space velocity is less than 1,000 hr$^{-1}$, a space time yield of acrylic acid as the targeted compound becomes low, whereas when it exceeds 8,000 hr$^{-1}$, the conversion is lowered.

The metal oxide catalyst as produced in the invention can also be applied to ammoxidation of propane and can synthesize acrylonitrile in a high yield. The ammoxidation condition substantially follows the foregoing vapor catalytic oxidation condition of propane.

The invention will be more specifically described below with reference to the Examples and Comparative Examples. Incidentally, in the following Examples 1 to 7 and Comparative Examples 1 to 2, the respective raw materials were blended such that all of proportions of the respective metals constituting the resulting metal oxide catalysts became the following values.

Mo/V/A/Nb=1.0/0.3/0.18/0.08

1.5 mL (about 2.2 g) of the catalyst as produced in each Example was charged in a 10-mmφ quartz-made reaction tube. The reaction tube was heated at 400° C., and a mixed gas containing 6.4% by volume of propane, 9.6% by volume of oxygen, 36.1% by volume of nitrogen and 47.7% by volume of steam was fed into the reaction tube at a space velocity of 3,924hr$^{-1}$, thereby producing acrylic acid.

Respective components as formed in the reaction product were subjected to composition analysis. By using the results of the composition analysis, a conversion of propane and a selectivity of acrylic acid (all of which are on a molar basis) were calculated according to the following expressions, and the performance of the used catalyst was evaluated from the values. The results are shown in Table 1. In Table 1, AA stands for acrylic acid; and P stands for propane.

Conversion of propane (%)=100×[(Fed propane)−(Unreacted propane)]/(Fed propane)

Selectivity of acrylic acid (%)=100×(Formed acrylic acid)/[(Fed propane)−(Unreacted propane)]

Yield of acrylic acid (%)=(Conversion of propane)×(Selectivity of acrylic acid)/100

EXAMPLE 1

In a ceramics-made pot for grinding having a volume of 500 mL, 2.01 g of a metallic tellurium powder (a mean particle size: 150 μm) and 2.6 g of distilled water were charged and mixed, and 25 zirconia balls having a size of 10 mm (ZrO$_2$: 95%, density: 6.0 g/cm$^3$) and 5 balls of the same material quality having a size of 20 mm were then charged therein. The foregoing pot was placed on two rotary rolls and subjected to grinding treatment by rotating at a rotational speed of 170 rpm for 24 hours.

A small amount of a sample was collected from an aqueous dispersion after grinding treatment (hereinafter referred to as "dispersion a"), and the particle size distribution of the tellurium powder was measured by using HORIBA, LA-500 Model, a laser diffraction type particle size distribution analyzer. A mode size representing a representative particle size was 2.0 μm. Incidentally, in the foregoing grinding step, a weight ratio of water to Te was 1.3.

Separately, in a 500-mL glass-made flask, 3.07 g of ammonium metavanadate, 15.45 g of ammonium molybdate, and 50 mL of distilled water were added and dissolved with stirring at the boiling temperature of water. To the resulting solution, the foregoing dispersion a and 40 g of distilled water were added, and the mixture was refluxed at the boiling temperature of water for one hour while rotating at a rotational speed of 500 rpm by a stirring machine, thereby obtaining a deeply blue reaction liquid (hereafter referred to as "reaction liquid b").

The flask having the foregoing reaction liquid b charged therein was cooled to 30° C. with ice water. On the other hand, 4.41 of oxalic acid and 1.16 g of niobic acid were dissolved in 70 mL of distilled water to prepare an aqueous solution of the ambient temperature, and this aqueous solution was then added to the foregoing reaction liquid b. The resulting mixed liquid was vigorously stirred for 10 minutes, and 2.5 g of ammonium nitrate was then mixed with this mixed liquid. Thereafter, the resulting mixture was heated for concentration and further evaporated to dryness at 120° C.

The resulting dried material was calcined in air at 300° C. for 5 hours. Thereafter, the resulting calcined material was further calcined at 600° C. for 2 hours in an inert atmosphere through which nitrogen was passed, thereby obtaining a metal oxide catalyst. The resulting catalyst was subjected to tablet making and further pulverized into from 16 to 30 meshes, and then used for production reaction of acrylic acid. The results are shown in Table 1.

EXAMPLE 2

A catalyst was prepared in the same manner as in Example 1, except that the amount of water to be used for the preparation of the dispersion a was changed to 5.0 g. A mass ratio of water to Te in grinding step was 2.5. Incidentally, as a result of measurement of the particle size distribution of the metallic Te particle after grinding, the mode particle size was found to be 2.6 μm.

By using the resulting catalyst, acrylic acid was produced under the same condition as in Example 1. The results are shown in Table 1.

EXAMPLE 3

A catalyst was prepared in the same manner as in Example 1, except that the amount of water to be used for the preparation of the dispersion a was changed to 13.0 g. A mass ratio of water to Te in grinding step was 6.5. Incidentally, as a result of measurement of the particle size distribution of the metallic Te particle after grinding, the mode particle size was found to be 8.8 μm.

By using the resulting catalyst, acrylic acid was produced under the same condition as in Example 1. The results are shown in Table 1.

EXAMPLE 4

A catalyst was prepared in the same operation as in Example 1, except that 2.5 g of ethanol was used in place of the water as used in the preparation of the dispersion a. A mass ratio of ethanol to Te in grinding step was 1.3. Incidentally, the particle size distribution of the metallic Te particle after grinding was measured. The mode particle size was found to be 3.2 μm.

By using the resulting catalyst, acrylic acid was produced under the same condition as -in Example 1. The results are shown in Table 1.

EXAMPLE 5

A catalyst was produced in the same operation as in Example 1, except that in the preparation of the dispersion a, a mixture of 0.5 g of aqueous solution of hydrogen peroxide having a concentration of 35% by mass and 5.0 g of distilled water was supplemented. A molar ratio of hydrogen peroxide to Te in grinding step was 0.33. The particle size distribution of the metallic Te particle after grinding was measured. The mode particle size was found to be 5.8 μm.

By using the resulting catalyst, acrylic acid was produced under the same condition as in Example 1. The results are shown in Table 2.

EXAMPLE 6

A catalyst was produced in the same manner as in Example 1, except that in the preparation of the dispersion a, a mixture of 1.57 g of aqueous solution of hydrogen peroxide having a concentration of 35% by mass. and 5.0 g of distilled water was supplemented. A molar ratio of hydrogen peroxide to Te in grinding step was 1.0. The particle size distribution of the metallic Te particle after grinding was measured. The mode particle size was found to be 3.9 μm.

By using the resulting catalyst, acrylic acid was produced under the same condition as in Example 1. The results are shown in Table 2.

EXAMPLE 7

A catalyst was produced in the same operation as in Example 1, except that in the preparation of the dispersion a, a mixture of 3.14 g of aqueous solution of hydrogen peroxide having a concentration of 35% by mass and 5.0 g of distilled water was supplemented. A molar ratio of hydrogen peroxide to Te in grinding step was 2.0. The particle size distribution of the metallic Te particle after grinding was measured. The mode particle size was found to be 2.3 μm.

By using the resulting catalyst, acrylic acid was produced under the same condition as in Example 1. The results are shown in Table 2.

EXAMPLE 8

A dispersion of Te was produced in the same operation as in Example 1, except that in the preparation of the dispersion a, not only the amount of the metallic Te powder was changed to 1.45 g, but also a mixture of 1.13 g of aqueous solution of hydrogen peroxide having a concentration of 35% by mass and 5.0 g of distilled water was supplemented. A molar ratio of hydrogen peroxide to Te in grinding step was 1.0. The particle size distribution of the metallic Te particle after grinding was measured. The mode particle size was found to be 5.8 μm.

In a 500-mL glass-made flask, 2.66 g of ammonium metavanadate, 3.0 g of ammonium molybdate, and 50 mL of distilled water were added and dissolved with stirring at the boiling temperature of water. To the resulting solution, the foregoing metallic tellurium dispersion was added, and the mixture was subjected to heat treatment for one hour. 12.45 g of ammonium molybdate was dissolved in the resulting reaction liquid, 1.4 g of 30% ammonia water was further dropped in the solution, and the reaction liquid then reached 60° C. after a lapse of several minutes with stirring. On the other hand, 5.89 g of oxalic acid and 2.32 g of niobic acid were dissolved in 160 mL of distilled water to prepare an aqueous solution of the ambient temperature, and this aqueous solution was added to the foregoing reaction liquid.

After vigorously stirring the resulting mixed liquid for 10 minutes, this mixed liquid was mixed with 3.5 g of ammonium nitrate. Thereafter, the mixture was heated for concentration and further evaporated to dryness at 120° C. by using a drying machine.

The resulting dried material was calcined in air at 320° C. for 1.5 hours. The resulting catalyst precursor was calcined in the absence of oxygen under the condition at 590° C. for 1.5 hours, thereby obtaining a metal oxide catalyst. This catalyst had a metal atomic ratio of components of Mo/V/Te/Nb of 1.0/0.25/0.13/0.16 (molar ratio).

The resulting catalyst was subjected to tablet making and further pulverized into from 16 to 30 meshes, and then used for production reaction of acrylic acid. As a result, a conversion of propane was 60.1%, a selectivity of acrylic acid was 80.5%, and a yield of acrylic acid was 48.45%, respectively.

COMPARATIVE EXAMPLE 1

To an aqueous dispersion of 2.01 g of an unground metallic Te particle (mean particle size: 150 μm) dispersed in 95 g of water, 15.45 g of ammonium molybdate and 3.07 g of ammonium metavanadate were added, and the mixture was heated. After the heating, all of the same operations as in Example 1 were followed, thereby producing a catalyst. By using this catalyst, acrylic acid was produced under the same condition as in Example 1. The results are shown in Table 1.

COMPARATIVE EXAMPLE 2

The step (1) for grinding metallic Te was omitted, and 15.45 g of ammonium molybdate, 3.07 g of ammonium metavanadate, and 4.62 g of telluric acid were directly heated and dissolved to obtain a reaction liquid b. After the heating, all of the same operations as in Example 1 were followed, thereby producing a catalyst. By using this catalyst, acrylic acid was produced under the same condition as in Example 1. The results are shown in Table 1.

COMPARATIVE EXAMPLE 3

15.45 g of ammonium molybdate was dissolved in 70 g of distilled water, into which was then suspended 2.01 g of a metallic Te powder (mean particle size: 150 μm) at room temperature. To this suspension, 4.7 g of 35% by mass aqueous solution of hydrogen peroxide [hydrogen peroxide/Te: 3.1 (molar ratio)] was added, and the mixture was heated at 70° C. with stirring. Following the heating, Te was dissolved so that the mixture ultimately became a colorless solution. To this solution, 3.07 g of ammonium metavanadate was added and dissolved, and the flask having this solution charged therein was cooled to 30° C. with ice water. Separately, an aqueous solution of the ambient temperature of 4.41 g of oxalic acid and 1.16 g of niobic acid dissolved in 70 mL of distilled water was prepared and mixed with the foregoing solution cooled to 30° C.

After vigorously stirring the resulting mixed liquid for 10 minutes, 2.5 g of ammonium nitrate was added to this mixed liquid and uniformly mixed. Thereafter, the mixture was heated for concentration and further evaporated to dryness at 120° C.

The resulting dried material was calcined in air at 300° C. for 5 hours. The resulting material was further calcined at 600° C. for 2 hours while passing nitrogen therethrough, thereby obtaining a catalyst. This catalyst had an atomic ratio of components of Mo/V/Te/Nb of 1.0/0.3/0.18/0.08. This catalyst was dried, subjected to tabletting, and further pulverized into from 16 to 30 meshes. By using the resulting catalyst, acrylic acid was produced under the same condition as in Example 1. The results are shown in Table 1.

TABLE 1

|  | Water/Te (mass ratio) | Conversion of P (%) | Selectivity of AA (%) | Yield of AA (%) |
|---|---|---|---|---|
| Example 1 | 1.3 | 40.0 | 74.5 | 34.3 |
| Example 2 | 2.5 | 49.2 | 75.6 | 37.2 |
| Example 3 | 6.5 | 47.9 | 74.8 | 35.8 |
| Example 4 | 1.3 | 51.2 | 72.1 | 36.9 |
| Comparative Example 1 | Not ground | 11.6 | 56.9 | 6.6 |
| Comparative Example 2 | Not ground | 29.6 | 57.9 | 17.1 |
| Comparative Example 3 | Not ground | 37.8 | 76.1 | 28.2 |

TABLE 2

|  | Water/Te (mass ratio) | Conversion of P (%) | Selectivity of AA (%) | Yield of AA (%) |
|---|---|---|---|---|
| Example 5 | 0.33 | 54.3 | 74.9 | 40.7 |
| Example 6 | 1.00 | 56.3 | 79.8 | 44.9 |
| Example 7 | 2.00 | 52.1 | 78.7 | 41.0 |

INDUSTRIAL APPLICABILITY

According to the production process of the invention, since a fine particle dispersion obtained by grinding metallic Te or Sb in the presence of water or an organic solvent is used as a raw material in the catalyst production, a metal oxide catalyst with high performance can be obtained with good reproducibility. By using this catalyst in the production of acrylic acid by vapor phase catalytic oxidation reaction of propane, it is possible to obtain acrylic acid in a high yield. Also, the present metal oxide catalyst can also be used for ammoxidation of propane.

The invention claimed is:

1. A process for producing a metal oxide catalyst represented by the following composition formula, comprising the following step (1), step (2), step (3) and step (4):

Step (1): grinding metal A to a fine particle dispersion in the presence of water without any of $Mo^{6+}$ compounds and $V^{5+}$ compounds to obtain an aqueous dispersion or grinding metal A to a fine particle dispersion in the presence of an organic solvent without any of $Mo^{6+}$ compounds and $V^{5+}$ compounds to obtain an organic solvent dispersion;

Step (2): adding a $Mo^{6+}$ compound and a $V^{5+}$ compound to said aqueous dispersion obtained in step (1) and heating to obtain a reaction liquid, or in the case where an organic solvent dispersion has been obtained in the step (1), substituting water for the organic solvent to obtain an aqueous dispersion and then adding a $Mo^{6+}$ compound and a $V^{5+}$ compound to the aqueous dispersion and heating to obtain a reaction liquid;

Step (3): adding metal B to the reaction liquid obtained in the step (2) to obtain a mixed liquid; and Step (4): evaporating to dryness and calcining the mixed liquid obtained in step (3) to obtain the composition formula:

$$MoV_iA_jB_kO_y$$ Composition formula:

wherein A is Te or Sb; B is at least one element selected from the group consisting of Nb, Ta, W, Ti, Zr, Re, Fe, Ni, Co, Sn, Tl, Cu, rare earth elements, and alkali metal elements; i and j are each from 0.01 to 1.5, and j/i is from 0.3 to 1.0; k is from 0.001 to 3.0; and y is the number to be determined by the oxidation state of other elements.

2. The process for producing a metal oxide catalyst according to claim 1, wherein hydrogen peroxide is used in addition to water or the organic solvent.

3. The process for producing a metal oxide catalyst according to claim 1, wherein the fine particle dispersion of the metal A after grinding has a mode size of not more than 20 μm.

4. A process for producing a metal oxide catalyst represented by the following composition formula, comprising the following step (1), step (2), step (3) and step (4):

Step (1): grinding metal A to a fine particle dispersion in the presence of water without any of $Mo^{6+}$ compounds and $V^{5+}$ compounds to obtain an aqueous dispersion or grinding metal A to a fine particle dispersion in the presence of an organic solvent without any of $Mo^{6+}$ compounds and $V^{5+}$ compounds to obtain an organic solvent dispersion;

Step (2): adding a $Mo^{6+}$ compound and a $V^{5+}$ compound to said aqueous dispersion obtained in step (1) and heating at 60° C. or higher for at least 10 minutes to obtain a reaction liquid, or in the case where an organic solvent dispersion has been obtained in the step (1), substituting water for the organic solvent to obtain an aqueous dispersion and then adding a $Mo^{6+}$ compound and a $V^{5+}$ compound to the aqueous dispersion and heating at 60° C. or higher for at least 10 minutes to obtain a reaction liquid;

Step (3): adding metal B the reaction liquid obtained in the step (2) to obtain a mixed liquid; and Step (4): evaporating to dryness and calcining the mixed liquid obtained in step (3) to obtain the composition formula:

$$MoV_iA_jB_kO_y$$ Composition formula:

wherein A is Te or Sb; B is at least one element selected from the group consisting of Nb, Ta, W, Ti, Zr, Re, Fe, Ni, Co, Sn, Tl, Cu, rare earth elements, and alkali metal elements; i and j are each from 0.01 to 1.5, and j/i is from 0.3 to 1.0; k is from 0.001 to 3.0; and y is the number to be determined by the oxidation state of other elements.

5. The process for producing a metal oxide catalyst according to claim 4, wherein in step (1), hydrogen peroxide is used in addition to water or the organic solvent.

6. The process for producing a metal oxide catalyst according to claim 4, wherein in step (2), the fine particle dispersion of the metal A after grinding has a mode size of not more than 20 μm.

7. A process for producing acrylic acid, by the vapor phase catalytic oxidation of propane in the presence of the metal oxide catalyst as produced by the process according to any one of claims 2 to 6.

8. A process for producing acrylonitrile, by subjecting propane to ammoxidation in the presence of the metal oxide catalyst as produced by the process according to any one of claims 2 to 6.

* * * * *